United States Patent [19]

Daher

[11] Patent Number: 5,922,351
[45] Date of Patent: Jul. 13, 1999

[54] LUBRICANTS FOR USE IN TABLETTING

[75] Inventor: Lawrence J. Daher, Elkhart, Ind.

[73] Assignee: Bayer Corporation, Morristown, N.J.

[21] Appl. No.: 08/127,433

[22] Filed: Sep. 27, 1993

Related U.S. Application Data

[63] Continuation-in-part of application No. 07/908,527, Jun. 29, 1992, Pat. No. 5,424,075, which is a continuation of application No. 07/676,165, Mar. 27, 1991, abandoned.

[51] Int. Cl.$^6$ .............................. A61K 9/46; A61K 9/20
[52] U.S. Cl. .................... 424/465; 424/464; 424/466; 514/960
[58] Field of Search ...................... 424/464, 465, 424/466, 479; 436/60; 514/960; 252/9, 10, 11; 106/38.2, 38.22, 38.7; 508/532, 539, 536

[56] References Cited

U.S. PATENT DOCUMENTS

| | | | |
|---|---|---|---|
| 3,506,756 | 4/1970 | Hoss . | |
| 3,518,343 | 6/1970 | Welsh et al. . | |
| 3,518,344 | 6/1970 | Welsh et al. . | |
| 3,518,345 | 6/1970 | Dines et al. . | |
| 3,518,346 | 6/1970 | Cox . | |
| 3,577,490 | 5/1971 | Welsh et al. . | |
| 3,577,491 | 5/1971 | Cox . | |
| 3,577,492 | 5/1971 | Welsh et al. . | |
| 3,584,099 | 6/1971 | Hoss . | |
| 3,619,462 | 11/1971 | Dines . | |
| 3,692,896 | 9/1972 | Tsumura et al. | 424/44 |
| 4,205,066 | 5/1980 | Hennart et al. | 424/84 |
| 4,455,416 | 6/1984 | Floyd et al. | 528/245 |
| 4,562,024 | 12/1985 | Rogerson | 264/117 |
| 4,851,390 | 7/1989 | Morishige | 514/44 |
| 5,358,655 | 10/1994 | Kruse et al. | 510/224 |
| 5,370,879 | 12/1994 | Masterson et al. | 424/490 |
| 5,424,075 | 6/1995 | Daher et al. | 424/465 |
| 5,445,827 | 8/1995 | Fritsch et al. | 424/465 |
| 5,468,516 | 11/1995 | Yamashita et al. | 427/180 |

FOREIGN PATENT DOCUMENTS 0 505 782   9/1992   European Pat. Off. .

OTHER PUBLICATIONS

Hackh's Chemical Dictionary, 4th. ed., edited by J. Grant, McGraw–Hill Book Company, New York, p. 541, 1969.

*Primary Examiner*—John Kim
*Attorney, Agent, or Firm*—Burns, Doane, Swecker & Mathis, L.L.P.

[57] ABSTRACT

The invention provides a number of new water soluble lubricants and lubricant formulations which facilitate the production of tablets. In particular calcium and potassium sorbates and micronized combinations of polyethylene glycol with calcium ascorbate or with trisodium citrate or mixtures thereof are useful as lubricants, particularly in tablet compositions containing ingredients where rapid dissolution in an aqueous environment is desired for activity or desired for aesthetic purposes. A method is provided for surface treating calcium sorbate with docusate sodium, Simethicone Emulsion, USP or with lecithin to provide particularly useful tablet lubricants. The above lubricant(s) and lubricant formulations have fewer limitations and improved functionality in comparison to standard lubricants presently known. In addition, the lubricant(s) provided may be used with known hydrophobic lubricants to decrease the amount of the hydrophobic lubricant required for lubrication.

7 Claims, No Drawings

LUBRICANTS FOR USE IN TABLETTING

RELATED APPLICATIONS

This application is a continuation-in-part of application Ser. No. 07/908,527,07, filed Jun. 29, 1992, now U.S. Pat. No. 5,424,075, which application is a continuation of application Ser. No. 07/676,165, filed Mar. 27, 1991, now abandoned, from which priority is claimed.

FIELD OF THE INVENTION

The invention relates to lubricants used in tabletting in general and to tabletting of water soluble active ingredients in particular.

BACKGROUND OF THE INVENTION

In order to compress a composition into tablets, lubrication of the tabletting machinery is generally required. Although it is possible to lubricate the dies and presses directly (external lubrication), the problems involved when tablets are to be prepared commercially at a high speed makes their use impractical. Therefore, most lubricants used are added to the formulation itself (internal lubrication). When a lubricant is added to the formulation, it must provide the necessary lubrication without interfering with the flowability or compressability of the formulation and without interfering with the release of the active ingredient. Many of the best lubricants are hydrophobic or water insoluble, for example calcium or magnesium stearate, talc, and vegetable oils; and for many formulations where rapid release of the active ingredient is not required, these lubricants are sufficient. However, lubrication of tablets where rapid dissolution is desired presents a particular problem, since hydrophobic lubricants may impede the release of the active ingredient(s) from the tablet. When the tablet is a pharmaceutical, this release of the active ingredient may be crucial to the onset of action and even to whether the ingredient elicits the desired response. In addition, when a tablet intended for dissolution in water prior to ingestion is prepared, e.g. an effervescent tablet, hydrophobic lubricants are generally avoided because their presence tends to leave an unsightly scum upon dissolution making the solution less palatable to the consumer. Therefore, there is a need for water soluble lubricants which may be used in general, but in particular for tabletting fast dissolving pharmaceuticals and/or nutritional supplements.

Although water soluble lubricants do not impede the release of active ingredient(s) from the tablet as hydrophobic lubricants can, they generally have poorer lubrication properties than the hydrophobic lubricants. Therefore, there has been a proliferation of compositions and processes providing soluble lubricants. Known soluble lubricants include: fumaric acid, adipic acid, boric acid, sodium benzoate, potassium benzoate, sodium propionate, sodium stearyl fumarate, sodium lauryl sulfate, magnesium lauryl sulfate, L-leucine and various polyethylene glycols ranging in (average) molecular weight from 4000 to 20000. There have been a number of patents related to lubricants for tabletting pharmaceuticals or nutritional supplement, including U.S. Pat. Nos. 3,566,491; 3,548,099; 3,518,346; 3,506,756; 3,518,343; 3,518,344; 3,518,345; 3,619,462; 3,577,490; and 3,577,492. Some of the lubricant formulations provided herein were disclosed in a copending patent applications containing inventions by the same inventor. This copending patent application was published on Sep. 30, 1992 as EP 0 505 872 A1.

In practice, all known soluble lubricants have significant limitations. The new lubricant(s) and lubricant formulation (s) provide herein have fewer such limitations.

SUMMARY OF THE INVENTION

It has been found that calcium and potassium sorbates are generally useful as lubricants and may be used as a sole tablet lubricant in a tablet composition or as colubricants with standard lubricants well known to those of skill in the art. Calcium sorbate may be used as received from the normal commercial sources (referred to herein as its "native state") or may be surface treated to increase its wettability with docusate sodium or with lecithin or to increase its lubricative capacity with Simethicone Eumlsion, U.S.P. Calcium and/or potassium sorbate or surface treated calcium sorbate, may also be used as a colubricant in combination with comicronized mixtures of polyethylene glycol and calcium ascorbate or with comicronized mixtures of polyethylene glycol and sodium citrate. In addition, a comicronized mixture of polyethylene glycol and sodium citrate may be used as a lubricant alone or in conjunction with one of the standard lubricants or in conjunction with a comicronized mixture of polyethylene glycol and calcium ascorbate. These lubricants and lubricant formulations provide the practitioner with a significant improvement in available lubricants for compressed tablets and are useful for a wide range of tablet compositions.

DETAILED DESCRIPTION OF THE INVENTION

The new lubricants and lubricant formulations of this invention are particularly important for tablet compositions intended for dissolution in water such as effervescent tablets and to tablet compositions, such as pharmaceuticals and/or nutritional supplements, from which the active ingredient should be released quickly into a body fluid in order to be adsorbed and to exhibit activity. Effervescent tablets which are commonly dissolved in water prior to ingestion should dissolve without residue or film formation, both for aesthetic reasons and to avoid trapping the active ingredient in the residue or film, which may result in delivery of less active ingredient than is expected. Swallow or "regular" tablets are commonly intended to be swallowed whole and with subsequent disintegration and absorption from a body fluid to deliver the active ingredient. In most cases such tablets preferably disintegrate rapidly thereby providing a large surface area from which the active ingredient dissolves into the body fluid. If a hydrophobic lubricant is used, those of skill in the art take care that the lubricant does not coat the composition particles prior to compression, which coating could make the particles generally hydrophobic and impede the release of the active ingredient(s). Such care may require special handling of the composition, usually by controlling the addition sequence and shortening time the lubricant is mixed with the rest of the ingredients. In contrast, the sole lubricants of this invention may be added directly to and mixed with the remaining ingredients, decreasing the number of steps required to prepare a formulation for tabletting. The lubricant formulations, once prepared, may also be added directly to and mixed with the remaining ingredients without special care. Although the new lubricants and lubricant formulations (the term "lubricants" is used generally herein to refer to both sole lubricants and lubricant formulations) are particularly applicable to tablet compositions containing water soluble active ingredients, the lubricants provided may also be used when unimpeded water solubility is not required.

Active Ingredients

The lubricants may generally be used with any active ingredient requiring tabletting, absent some chemical incompatibility. Effervescent formulations commonly contain analgesics, antacids, decongestants, antihistamines and/or expectorants. In addition, the whole gamut of pharmaceuticals may be tabletted with the lubricants provided, including but not limited to, those listed above, $H_2$ blockers, antibiotics, sedatives, hypnotics and migraine preparations. Nutritional supplements such as vitamins and minerals, herbals and other dietary supplements may also be tabletted with these lubricants. Many of these ingredients are water soluble and therefore the lubricants provided have particular advantages.

Other Ingredients

In addition to the active ingredient(s), other tabletting ingredients, well known to those of skill in the art may be used as needed. All such ingredients in pharmaceuticals and nutritionals must support the tablet function of delivering and releasing the active ingredient(s) to the body in the intended manner. These other ingredients commonly include colors, flavors, diluents, binders, fillers and disintegrants. For effervescent tablets, all such ingredients should be water soluble.

Lubricants

Lubricants are generally chosen by balancing the need for lubrication of the composition during tabletting with the need to find a lubricant which does not impede the release and/or availability of the active ingredient(s). The lubricants or lubricant formulations provided may be used as the sole lubricant, or may be used in combination with other lubricants well known to those of skill in the art of compressed tabletting. They may be advantageously used in combination with water insoluble lubricants. Such water insoluble lubricants generally provide the best tablet lubrication, but because of the problems of dissolution and drug release, must be used in the smallest amount possible. The combination of the lubricants or lubricant formulations provided herein with insoluble, hydrophobic lubricants, allows the amount of the hydrophobic lubricant to be decreased.

Lubricant concentrations are given as a weight percent of tablet composition. This is generally the minimum amount which has been shown to provide useful lubrication. However, lower amounts of about 0.5 weight percent less may be used and higher amounts may be used up to the point at which the lubricant interferes with either the tabletting or with the disintegration and release of the active ingredient. Given the disclosure and examples provided herein, those of skill in the art will be able to use the lubricants provided, advantageously, for a wide range of tablet formulations particularly for pharmaceutical and nutritional supplements.

Potassium Sorbate

Potassium sorbate has been found to act as a water soluble lubricant which has both antiadherent and antifrictional lubricant properties and therefore may be used as the sole lubricant. In general, it has been found that it provides lubrication at about 3% by weight of the tablet composition. In addition, it may be used in combinations provided herein as lubricant formulations. It may also be used with standard lubricants known to those of skill in the art. When used in combination, the amount of potassium sorbate and the amount of the standard lubricant will be decreased.

Calcium Sorbate

Calcium sorbate has been found to act as a water soluble lubricant which has both antiadherent and antifrictional lubricant properties and therefore may be used as the sole lubricant. In general, it has been found that it provides lubrication at about 5% by weight of the tablet composition. In addition, it may be used in combinations provided herein as lubricant formulations. It may also be used with standard lubricants known to those of skill in the art. When used in combination, the amount of calcium sorbate and the amount of the standard lubricant will be decreased.

Preferably, calcium sorbate is surface treated with docusate sodium, Simethicone Emulsion USP (sometimes referred to as polydimethyl silicone) or lecithin as described in Examples 1 to 4. The surface treated calcium sorbate may be used in lower amounts, generally as low as 4% by weight. When mixtures of the surface treated calcium sorbate are used, the amount used may be as low as 1.5 to 2.5% by weight.

Calcium sorbate, in its native state or as surface treated, may also be used with the comicronized mixture of polyethylene glycol and trisodium citrate and/or with the comicronized mixture of polyethylene glycol and calcium ascorbate, described below.

Polyethylene Glycol

"Polyethylene glycol" as referred to herein is a polyethylene glycol which has a molecular weight average from about 4000 to about 20,000 (referred to collectively herein as PEG). Polyethylene glycol 8000 (PEG 8000) is preferred and is used as an example of the class throughout this disclosure. PEG has some of the physical properties of a wax, yet is water soluble. Unfortunately, since PEG is not a high potency lubricant, it must be used at relatively high concentrations in tablet formulations in order to provide lubrication. Thus, although it known to be useful as a tablet lubricant in its own right, and can be used alone; because it is a polymer, tablets prepared with the amounts required for lubrication tend to dissolve rather slowly. The slow dissolution may impede the onset of activity, and also makes it generally undesirable as a lubricant for effervescent tablets. Therefore it is generally desirable to reduce the concentration of PEG in a tablet composition.

Polyethylene Glycol Comicronized with Sodium Citrate or with Calcium Ascorbate

It has been found that, if PEG, preferably PEG 8000, is spread in a very thin layer over a large surface area of carrier material, such as anhydrous trisodium citrate (referred to herein as trisodium citrate, and is also sometimes referred to as "trisodium citrate USP") or calcium ascorbate, the resulting lubricant formulation has the advantages of PEG without its coexisting and troublesome physical properties. This spreading is advantageously accomplished through comicronization of a minor portion of PEG along with a major portion of carrier and the combination appears to take on the physical properties of the carrier while retaining the lubricating properties of PEG. Neither trisodium citrate nor calcium ascorbate have lubricant properties of their own. However, though the interaction between these carriers and PEG is not understood, these carriers appear to contribute some functionality to the lubricant properties of the micronized mixtures, and the formulations function better as lubricants than PEG alone. The lubricant formulation produced is conveniently used and may be added directly to the other tablet ingredients, mixed and compressed. A ratio of about 6 parts PEG to 94 parts of carrier is preferred and when a mixture of the two comicronized mixtures is used, a 1:1 ratio is suggested.

Preparation of Lubricants

Sole Lubricants

While tabletted ingredients are commonly granular and have a coarse particle size to impart good flow properties to the composition, lubricants in general, including the lubricants calcium and potassium sorbate and the other lubricant formulations provided herein, are preferably added to the remaining tablet composition in a form having a very fine particle size. This can be accomplished in a variety of ways well know to those of skill in the art and is often accomplished by ball milling.

Surface Treatment

Calcium sorbate provides even better lubrication when surface treated with Simethicone Emulsion USP. (Simethicone Emulsion USP is sometimes referred to as polydimethyl siloxane or even just simethicone.) In addition it has been found that calcium sorbate, surface treated with lecithin or docusate sodium, imparts satisfactory lubrication and also improves the rate of dissolution of the finished tablet. Generally a solution of the surface treatment component is added to the calcium sorbate while mixing, the calcium sorbate is recovered and dried. Commonly, 0.2% by weight of the surface treatment component to the total lubricant weight is sufficient to provide improved properties. However, this amount may be adjusted, up or down, depending on the needs of the particular tablet composition.

Comicronization

Comicronization to provide preferred lubricant formulations is illustrated in Examples 5 and 6. The lubricant combinations provided herein are advantageously prepared in an fluid energy mill, (also called an air mill or a micronizer) in which particle size reduction is accomplished through high speed impact of feed material particles with each other as they are carried through the mill by a high velocity gas stream. The impact causes a shattering of hard materials and a smearing of soft materials. The mixture achieved is referred to as "comicronized" herein. It is hypothesized, but not relied upon, that the impact of the mixture of particles of PEG 8000 and anhydrous trisodium citrate or calcium ascorbate results in a size reduction of the hard carrier, anhydrous trisodium citrate or calcium ascorbate, along with the concomitant smearing of relatively softer PEG 8000 over the surface of the small and harder particles of carrier material. Scanning electron micrographs seem to confirm this hypothesis, but the evidence is based upon the relatively smoother appearance of the mixed comicronized particles compared to rougher looking micrographs of anhydrous trisodium citrate alone. Although specific settings are provided in the Examples for a specific micronizer, those setting are equipment specific and may be modified when other equipment is used. Such modification is within the skill of those knowledgeable in the art of tabletting given the disclosure herein.

In general the lubricant or lubricant formulation is added to the other tablet ingredients directly, the ingredients are mixed thoroughly, and then compressed into tablets. The tablets may be packaged as desired. For example they may be bottled or sealed into paper or aluminum foil. Particular equipment is mentioned in the Examples, but other equipment, and equipment settings, which provide the same end result may be used.

Use of the Lubricants and Lubricant Formulations

The use of the lubricants and lubricants formulations provided here is specifically illustrated in Examples 7 to 13. Examples 7 to 9 and 11 illustrate their use in effervescent formulations, which have particular tabletting lubrication problems due to the requirement of fast, complete dissolution in water prior to ingestion. Examples 10, 12 and 13 illustrate the use of the lubricants and lubricant formulations in swallow tablets (i.e. tablets designed for ingestion, whole, sometimes known as swallowable tablets and often thought of as regular tablets). Given the guidance in this specification and particularly in the Examples, one of ordinary skill in the art of tabletting compression will be able to use the lubricant(s) and lubricant formulations provided in any number of tablet compositions requiring lubrication. It has been found that preferred lubricant and lubricant formulations are from a. about 3% by weight potassium sorbate;
b. about 5% by weight calcium sorbate;
c. about 4% by weight of surface treated calcium sorbate;
d. about 1.5% to 2.5% by weight of each component if a mixture of surface treated calcium sorbates are used or if surface treated calcium sorbate is used with one of the comicronized lubricants provided herein;
e. from about 4 to 14% by weight of the comicronized mixture of trisodium citrate (94%) and PEG 8000 (6%);
f. about 5 to 7%, preferably 6%, by weight of each of the comicronized mixtures of trisodium citrate (94%) and PEG 8000 (6%) and comicronized calcium ascorbate (94%) and PEG 8000 (6%).

In general an effervescent tablet may be prepared by mixing a effervescent couple (an edible organic acid and an alkaline metal salt of a carbonate, bicarbonate or an acid anhydride) with one of the lubricants or lubricant formulations provided herein, blending and compressing the mixture into tablets. A common effervescent couple is composed of citric acid and sodium bicarbonate. When a stoichiometric excess of bicarbonate is used the formulation will function, after ingestion in water solution, as an antacid. A high neutralizing capacity as indicated by testing according to USP XXII for an antacid may be easily achieved in this manner. There are many effervescent formulations well known to those of skill in the art of effervescent tabletting which may be improved with the lubricants and lubricant formulations provided herein.

Swallow tablets may also be advantageously prepared with the lubricants provided herein. Commonly the tablet ingredients may be prepared in a granulation and the lubricant and additional components such as a tablet disintegrant like crospovidone or cornstarch, or a tablet binder like silicon dioxide or alpha cellulose are blended and compressed by standard methods well known to those of skill in the art without special handling.

The following examples disclose preferred embodiments of the invention, but do not limit the applicability of the invention which is solely defined by the claims.

EXAMPLES

Example 1

Calcium Sorbate, Surface Treated with Docusate Sodium

A suspension of calcium sorbate was prepared by adding a solution of 110 grams of calcium chloride in 300 ml. of water to a solution of 300 grams of potassium sorbate in 1000 ml. of water, with mixing. About 25 drops of a 50% solution of docusate sodium (approximately 0.6 grams of the 50% solution) was added to the suspension, and mixed. The calcium sorbate was recovered, washed with a dilute solution of docusate sodium and dried.

Example 2

Calcium Sorbate 99.8%, Surface Treated with Docusate Sodium 0.2%

A surface treating solution of about 2 grams of a 50% solution of docusate sodium, U.S.P. in 198 grams of water was prepared. With the mixer running, the surface treating solution was added to 500 grams of calcium sorbate powder in a weight /weight ratio of about 2:5, along with enough water to thoroughly dampen the powder. The damp powder mixture produced was dried and screened.

Example 3

Calcium Sorbate 99.8%, Medical Antifoam C 0.2%

6.7 grams of Medical Antifoam C Emulsion from Dow Corning, Midland, Michigan (contains: 30% Simethicone U.S.P., 1.6% Methylcellulose U.S.P., 0.075% Sorbic Acid U.S.P., and Water) was added to about 294 grams of water, and mixed until the emulsion was fully dispersed. The surface treating emulsion was added to calcium sorbate powder in a weight/ weight ratio of about 3:10, with the mixer running, to produce a dampened powder mixture. The dampened powder was dried overnight and screened.

Example 4

Calcium Sorbate 99.8%, surface treated with Lecithin 0.2%

An aqueous dispersion of 6 grams of lecithin, N.F. in 294 grams of water was prepared with heating and mixing. The lecithin dispersion was added to calcium sorbate powder in a weight/weight ratio of about 3:10 with mixing, along with an additional amount of water to produce a thoroughly dampened powder. The dampened powder produced was dried overnight and screened.

Example 5

Anhydrous Trisodium Citrate 94%, comicronized with Polyethylene Glycol 8000 6%

A mixture of 1880 grams of Sodium Citrate, U.S.P. and 120 grams of Polyethylene Glycol 8000, N.F. was processed through a 4" air mill, using an air pressure feed rate setting of 16 pounds per square inch (psig) and an air pressure processing setting of 85 psig.

Example 6

Calcium Ascorbate 94%, comicronized with Polyethylene Glycol 8000 6%

A mixture of 1880 grams of Calcium Ascorbate, F.C.C. and 120 grams of Polyethylene Glycol 8000, N.F. was comicronized in the same manner as in Example 5.

Example 7

Potassium Sorbate as a Lubricant in an Effervescent Tablet Formula

One part finely powdered potassium sorbate was mixed with about 21 parts sodium bicarbonate and passed through a # 24 mesh U.S. Standard screen. The screened mixture was then screened with about 10 parts citric acid and the final mixture blended and compressed into tablets. The tablets may be sealed into a plain paper and aluminum laminated foil.

Example 8

Calcium Sorbate as a Lubricant in an Effervescent Tablet Formula.
Effervescent Ibuprofen and Ranitidine Tablet

| mg./tab. | |
|---|---|
| 396 | Ibuprofen/Sodium Citrate, Granulation |
| 114 | Ranitidine/Sodium Citrate, Granulation |
| 1600 | Sodium Bicarbonate |
| 1300 | Citric Acid/Mannitol, Granulation |
| 180 | Calcium Sorbate, finely powdered |
| 3590 | Total |

Ibuprofen and ranitidine were granulated separately with trisodium citrate, dihydrate. Citric acid was granulated with mannitol. These granulations, and the remaining ingredients were combined, mixed and compressed.

Example 9

Calcium Sorbate Surface Treated with Docusate Sodium as a lubricant in Effervescent Tablet Formula
Effervescent Ranitidine Tablet

| mg./tab. | |
|---|---|
| 14 | Ranitidine Hydrochloride |
| 1916 | Sodium Bicarbonate |
| 1000 | Citric Acid, Anhydrous, Milled |
| 122 | Calcium Sorbate, Surface Treated (Example 1) |
| 3052 | Total |

Ranitidine Hydrochloride and calcium sorbate, surface treated with docusate sodium and finely powdered as shown in Example 1, were mixed and screened. The citric acid and sodium bicarbonate were mixed and screened. Both mixtures were added to a mixer, blended and compressed.

Example 10

Anhydrous Trisodium Citrate 94%, Polyethylene Glycol 6%, as a lubricant in Swallow Tablet Formula.
Buffered Sodium Ibuprofen Tablet

| mg./tab. | |
|---|---|
| 269 | Sodium Ibuprofen, Granulation |
| 100 | Starch 1500 |
| 70 | Citric Acid, Anhydrous, Milled |
| 408 | Trisodium Citrate, Anhydrous, Granulation |
| 100 | Comicronized Anhydrous Trisodium Citrate/Polyethylene Glycol (Example 5) |
| 53 | Cellulose, Powdered, N.F. |
| 1000 | Total |

The starch, citric acid, comicronized trisodium citrate/PEG prepared as shown in Example 5, and cellulose were screened. The sodium ibuprofen and the trisodium citrate granulations were added and the resulting composition mixed and compressed into tablets.

Example 11

Anhydrous Trisodium Citrate 94%, Polyethylene Glycol 8000 6%; along with Calcium Ascorbate 94%, Polyethylene Glycol 8000 6%, as a lubricant in Effervescent Tablets
Effervescent Ranitidine Tablet

| mg./tab. | |
|---|---|
| 657 | Sodium Bicarbonate |
| 1264 | Citric Acid/Mannitol, Granulation |
| 228 | Ranitidine/Sodium Citrate, Granulation |
| 145 | Comicronized anhydrous trisodium Citrate/Polyethylene Glycol (Example 5) |
| 145 | Comicronized calcium ascorbate/Polyethylene Glycol (Example 6) |
| 2439 | Total |

The above ingredients were weighed, screened, mixed and compressed into tablets.

Example 12

Anhydrous Trisodium Citrate 94%, Polyethylene Glycol 8000 6%; along with Calcium Sorbate, Surface Treated with Docusate Sodium as a lubricant in a Swallow Tablet Buffered Sodium Ibuprofen Tablet

| mg./tab. | |
|---|---|
| 792 | Sodium Ibuprofen, Granulation |
| 70 | Sodium Citrate/Starch 1500, Granulation |
| 140 | Crospovidone XL-10 |
| 50 | Comicronized anhydrous trisodium Citrate/Polyethylene Glycol (Example 5) |
| 16 | Calcium Sorbate, surface treated with Docusate Sodium (Example 2) |
| 5 | Silicon Dioxide, Fumed |
| 1073 | Total |

Weigh, screen and mix all the above ingredients and compress into tablets.

Example 13

Anhydrous Trisodium Citrate 94%, Polyethylene Glycol 8000 6%; along with Calcium Sorbate, Surface Treated with Lecithin, and Calcium Sorbate, Surface Treated with Medical Antifoam C, as a Lubricant in a Swallow Tablet Formula.

Buffered Sodium Ibuprofen Tablet

| mg./tab. | |
|---|---|
| 296.2 | Sodium Ibuprofen, Granulation |
| 80.0 | Citric Acid Anhydrous, Milled |
| 508.0 | Trisodium citrate, Anhydrous, Milled |
| 60.0 | Comicronized anhydrous trisodium citrate/Polyethylene Glycol (Example 5) |
| 25.0 | Calcium Sorbate surface treated with Lecithin (Example 4) |
| 25.0 | Calcium Sorbate, surface treated (Example 3) |
| 994.2 | Total |

Weigh and mix all the above ingredients and compress into tablets.

It should be understood that many modifications and variations can be made in the proportions and components used herein without departing from the spirit and scope of the invention, which is solely defined by the claims.

What is claimed is:

1. A composition of matter comprising a compressed solid, wherein said compressed solid comprises an effective amount of a lubricating agent selected from the group consisting of: (a) potassium sorbate, (b) calcium sorbate, (c) a comicronized mixture of polyethylene glycol 8000 with a co-agent selected from the group consisting of anhydrous trisodium citrate, calcium ascorbate and mixtures thereof, and (d) mixtures of (a)–(c).

2. The composition of claim 1, wherein said lubricating agent comprises potassium sorbate.

3. The composition of claim 1, wherein said lubricating agent comprises calcium sorbate.

4. The composition of claim 3, wherein said calcium sorbate is surface treated with a component selected from the group consisting of docusate sodium, an emulsion of simethicone, lecithin and mixtures thereof.

5. The composition of claim 1, wherein said lubricating agent comprises a comicronized mixture of polyethylene glycol 8000 with a co-agent selected from the group consisting of anhydrous trisodium citrate, calcium ascorbate and mixtures thereof.

6. The composition of claim 1, wherein said compressed solid comprises a tablet.

7. The composition of claim 6, wherein said compressed solid comprises an effervescent tablet.

* * * * *